United States Patent
Mewshaw

Patent Number: 5,663,194
Date of Patent: Sep. 2, 1997

[54] CHROMAN-2-YLMETHYLAMINO DERIVATIVES

[76] Inventor: Richard E. Mewshaw, 21 Boxwood Dr., South Brunswick, N.J.

[21] Appl. No.: 684,521

[22] Filed: Jul. 19, 1996

Related U.S. Application Data

[60] Provisional application No. 60/001,418 Jul. 25, 1995.
[51] Int. Cl.$^6$ .......................... A61K 31/35; C07D 311/58
[52] U.S. Cl. ............................................. 514/456; 549/407
[58] Field of Search ............................ 549/407; 514/456

[56] References Cited

U.S. PATENT DOCUMENTS

| | | | |
|---|---|---|---|
| 4,321,270 | 3/1982 | Sundeen | 424/267 |
| 5,126,367 | 6/1992 | Stack et al. | 514/452 |
| 5,137,901 | 8/1992 | Junge et al. | 514/373 |
| 5,318,988 | 6/1994 | Schohe-Loop et al. | 514/458 |
| 5,371,094 | 12/1994 | Heine et al. | 514/323 |

FOREIGN PATENT DOCUMENTS

| | | |
|---|---|---|
| 0325964 | 8/1989 | European Pat. Off. |
| 0334429 | 9/1989 | European Pat. Off. |
| 0369874 | 5/1990 | European Pat. Off. |
| 9505383 | 2/1995 | WIPO |

OTHER PUBLICATIONS

Indian Journal of Chemistry, 20B, 12, 1063–1067, Dec. 1981.

Primary Examiner—Johann Richter
Assistant Examiner—Laura L. Stockton
Attorney, Agent, or Firm—Richard K. Jackson

[57] ABSTRACT

Described herein are compounds of the formula:

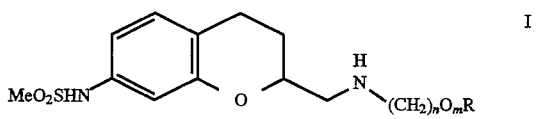

in which n is 1, 2 or 3; m is 0 or 1; and R is a substituted or unsubstituted phenyl group in which the substitutents are, independently, one or two members selected from the group consisting of alkyl, hydroxy, halo or amino groups or R is alkyl of 1 to 6 carbon atoms or hydroxyalkyl of 1 to 6 carbon atoms; or a pharmaceutically acceptable salt thereof, which are inhibitors of dopamine synthesis and release, and are useful in the treatment of schizophrenia, Parkinson's Disease, Tourette's Syndrome, alcohol addiction, cocaine addiction, and addiction to analagous drugs.

11 Claims, No Drawings

CHROMAN-2-YLMETHYLAMINO DERIVATIVES

BACKGROUND OF INVENTION

This application claims the benefit of U.S. Provisional Application No. 60/001,418, filed Jul. 25, 1995.

Efforts to induce antipsychotic activity with dopamine autoreceptor agonists have been successful (Corsini et al. Adv. Biochem. Psychopharmacol 16, 645–648, 1977; Tamminga et at. Science 200, 567–568, 1978; and Tamminga et al. Psychiatry 398–402, 1986). A method for determining intrinsic activity at the dopamine $D_2$ receptor was recently reported [Lahti et al., Mol. Pharm. 42, 432–438, (1993)]. Intrinsic activity is predicted using the ratio of the "low-affinity agonist" (LowAg) state of the receptor and the "high-affinity agonist" (HighAg) state of the receptor, i.e. LowAg/HighAg. These ratios correlate with the agonist, partial agonist, and antagonist activities of a given compound, which activities characterize a compounds ability to elicit an antipsychotic effect.

DESCRIPTION OF THE INVENTION

In accordance with this invention, there is provided a group of compounds which are useful antipsychotic agents. The compounds of this invention are essentially free from extrapyramidal side effects (EPS). The compounds of this invention are selective autoreceptor agonists, functioning primarily to activate only autoreceptors versus postsynaptic $D_2$ dopamine receptors). As such, they provide functional modulation of dopamine systems of the brain without the excessive blockade of the postsynaptic dopamine receptors, which have been observed to be responsible for the serious side effects frequently exhibited by agents found otherwise clinically effective for treatment of schizophrenia. Activation of the dopamine autoreceptors results in reduced neuronal firing a well as inhibition of dopamine synthesis and release and therefore provide a means of controlling hyperactivity of the dopaminergic systems.

More specifically, the compounds of this invention are depicted by the following Formula I:

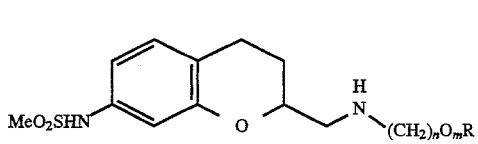

I in which n is 1, 2 or 3;

m is 0 or 1; and

R is a substituted or unsubstituted phenyl group in which the substitutents are, independently, one or two members selected from the group consisting of alkyl of 1 to 6 carbon atoms, hydroxy, halo or amino groups or R is alkyl of 1 to 6 carbon atoms or hydroxyalkyl of 1 to 6 carbon atoms; or a pharmaceutically acceptable salt thereof. Preferably, R is phenyl, tolyl or aminophenyl and most preferred are those compounds in which n is 1; m is 0 and R is phenyl or tolyl.

The pharmaceutically acceptable salts are those derived from such organic and inorganic acids as: acetic, lactic, citric, fumaric, tartaric, succinic, maleic, malonic, oxalic, hydrochloric, hydrobromic, phosphoric, nitric, sulfuric, methanesulfonic, methylbenzene sulfonic, and similarly known acceptable acids. The compounds of this invention contain an asymmetric carbon atom and therefore appear as racemic mixtures which are readily resolved into their pure enantiomers by conventional means.

The compounds of Formula I are prepared by the overall sequence as follows:

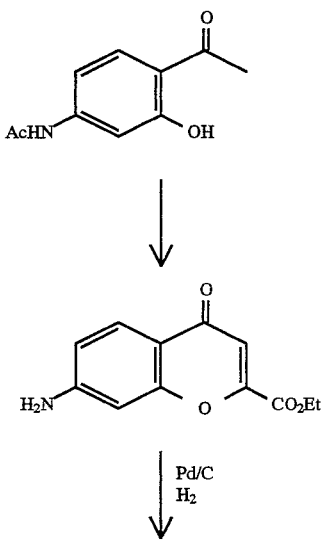

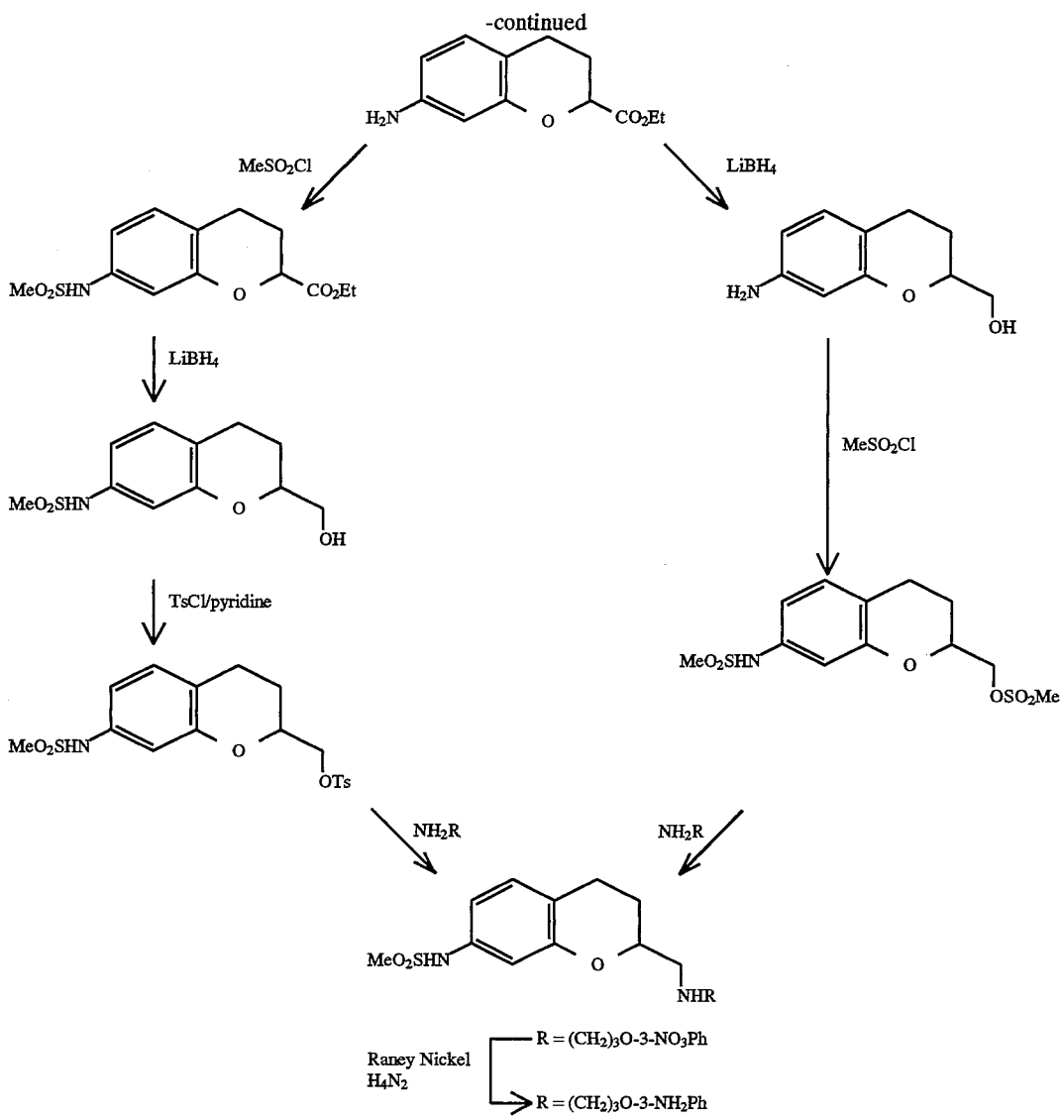

Specific exemplification of the production of representative compounds of this invention is given in the following examples:

EXAMPLE 1

N-(2-{[3-(3-Amino-phenoxy)-propylamino]-methyl}-chroman-7-yl)-methanesulfonamide A mixture of N-[4-acetyl-3-hydroxyphenyl)acetamide (24.1 g, 0.125 mol) and diethyl oxalate (47.5 g, 0.33 mol) in absolute ethanol (200 mL) was added to a solution of sodium ethoxide (14 g sodium in 300 mL absolute ethanol). The reaction was heated to reflux for 2 hours and allowed to cool to room temperature then poured into water (500 mL) and methylene chloride (1500 mL). The aqueous layer was made slightly acidic using 6N hydrochloric acid. The organic layer separated and the aqueous layer washed again using methylene chloride (500 mL). The combined organic layers were dried over anhydrous magnesium sulfate, filtered, and the solvent removed under vacuum. The solid material (35.8 g) was dissolved in ethanol (350 mL) and concentrated hydrochloric acid (6 mL) was added. The solution was heated to reflux for 1 day, removed from heat and allowed to stand for 2 days. The orange solid was filtered to afford 17 g of ethyl 7-amino-4-oxo-4H-1-benzopyran-2-carboxylate. The mother liquor was concentrated to afford another 4.94 g of desired product. Yield 75.6%, $^1$H NMR (DMSO-$d_6$) δ 1.32 (3H, t, J=7.25 Hz, CH$_2$CH$_3$,), 4.34 (2H, q, J=7.03 Hz, CH$_2$CH$_3$), 6.50 (2H, bs, NH$_2$), 6.53 (1H, d, J=1.98 Hz, =CH), 6.69 (1H, dd, J=8.78, 1.98 Hz, ArH), 6.71 (1H, s, ArH), 7.68 (1H, d, J=8.78 Hz, ArH); MS (EI) m/z, 233 (M+).

To a solution of ethyl 7-amino-4-oxo-4H-1-benzopyran-2-carboxylate (2.4 g, 10.3 mmol) in acetic acid (40 mL) was added 10% Pd/carbon and the mixture was hydrogenated on a Parr hydrogenator at 50 psi for five days. The catalyst was filtered through Celite® and the acetic acid was removed under high vacuum. The crude product chromatographed (30% ethyl acetate-hexane) to afford 1.27 g of ethyl (R,S)-3,4-Dihydro-7-amino-2H-1-benzopyran-2-carboxylate as a yellow oil (55.8%): IR (film) 3400, 2930, 1750, and 1630 cm–1; MS m/e, 221 (M+).

To a solution of ethyl (R,S)-3,4-dihydro-7-amino-2H-1-benzopyran-2-carboxylate (1.47 g, 6.64 mmol) in tetrahydrofuran (25 mL) at 0° C. was added a solution of lithium borohydride (7 mL of 2.0M) and the solution was then allowed to warm to room temperature. The reaction was quenched after 1.5 hours by the cautious addition of methanol (5 mL) and the reaction mixture was stirred for another 2 hours. The reaction mixture was diluted with ethyl acetate (300 mL) and washed with water (2×60 mL). The aqueous layer was washed again with ethyl acetate (100 mL) and the combined layers were dried over anhydrous magnesium sulfate, filtered, and the solvent was removed under vacuum. Purification by chromatography (50% ethyl acetate-hexane) afforded 892 mg (82.3%) of (R,S)-3,4-dihydro-7-amino-2H-1-benzopyran-2-methanol as a white solid, mp 89°–90° C.

Elemental analysis for $C_{10}H_{13}NO$ Calc'd: C, 67.02; H, 7.31; N, 7.82 Found: C, 66.94; H, 7.33; N, 7.94

To a solution of (R,S)-3,4-dihydro-7-amino-2H-1-benzopyran-2-methanol (810 mg, 4.96 mmol) in dry methylene chloride (20 mL) containing pyridine (4 eq) at 0° C. was added methanesulfonyl chloride (1.42 g, 12.4 mmol) and the solution was allowed stirred for 1.5 hours while waning to room temperature. The reaction was poured into 1N hydrochloric acid (100 mL) and extracted with methylene chloride (2×100 mL). The organic layer was washed with 1N hydrochloric acid (50 mL), water (50 mL), dried over anhydrous magnesium sulfate, filtered, and the solvent removed under vacuum. Purification by chromatography (50% ethyl acetate-hexane) afforded 1.48 g of (R,S)-3,4-dihydro-(7-sulfonamide)-2H-1-benzopyran-2-[methyl-(methanesulfonate)] as a white foam (90.0%): IR (film) 3290, 3050, 2950, 1630 and 1600 cm−1; MS m/e, 335 (M+).

A mixture of (R,S)-3,4-dihydro-(7-sulfonamide)-2H-1-benzopyran-2-methyl methylsulfonate (128 mg, 0.38 mmol), 3-(3-nitro-phenoxy)-1-aminopropane (374 mg, 1.91 mmol), potassium carbonate (132 mg, 2.5 mmol), and 20 mg of sodium iodide in dry DMF were heated to 80° C. for 16 hours. The reaction mixture was poured into diethyl ether (150 mL) and extracted with water (2×100 mL), washed with brine, dried over anhydrous magnesium sulfate, filtered, and the solvent removed under vacuum. Chromatography (3% methanol-methylene chloride) afforded 68 mg of N-(2-{[3-(3-nitro-phenoxy)-propylamino]-methyl}-chroman-7-yl)-methanesulfonamide (41.1%): MS m/e, 436 (M+).

To a mixture of N-(2-{[3-(3-nitro-phenoxy)-propylamino]-methyl}-chroman-7-yl)-methanesulfonamide and hydrazine in ethanol at 5° C. was added Raney nickel (400 mg). After 0.5 hour another portion of Raney nickel (300 mg) was added and the reaction was heated to reflux for 1 hour. The catalyst was filtered and the solvent removed to afford N-(2-{[3-(3-amino-phenoxy)-propylamino]-methyl}-chroman-7-yl)-methanesulfonamide in 69.9% yield. The (2:1)oxalate, hemihydrate was prepared from tetrahydrofuran and triturated in methanol, mp 183°–185° C.

Elemental analysis for $C_{20}H_{27}N_3O_4S.2(COOH)_2.0.5H_2O$ Calc'd: C, 48.48; H, 5.43; N, 7.07 Found: C, 48.53; H, 5.36; N, 7.05

This general procedure, without the final reduction step, utilizing 3-aminopropanol and 3-aminopropane afforded:

(1b) N-{2-[(3-Hydroxy-propylamino)-methyl]-chroman-7-yl}-methansulfonamide as the oxalate salt, mp 164°–165° C.

Elemental analysis for $C_{14}H_{22}N_2O_4S.(COOH)_2$ Calc'd: C, 47.52; H, 5.98; N, 6.93 Found: C, 47.32; H, 6.05; N, 6.79

(1c) N-(2-Propylaminomethyl-chroman-7-yl)-methanesulfonamide as the oxalate, hemihydrate, mp 204°–205° C.

Elemental analysis for $C_{14}H_{22}N_2O_3S.(COOH)_2.0.5H_2O$ Calc'd: C, 48.35; H, 6.34; N, 7.05 Found: C, 47.95; H, 5.91; N, 7.04

EXAMPLE 2

N-[2-(Benzylamino-methyl)-chroman-7-yl]-methanesulfonamide

To a solution of ethyl (R,S)-3,4-dihydro-7-amino-2H-1-benzopyran-2-carboxylate (2.5 g, 11.2 mmol) in dichloroethane (20 mL) containing pyridine (6 mL) at 5° C. was added methanesulfonyl chloride (1.3 g, 13.6 mmol). The reaction was allowed to stir for 20 min than poured in water (80 mL) and washed with 1N aqueous hydrochloride (2×100 mL), and water (100 mL). The organic layer was dried over anhydrous magnesium sulfate, filtered, and the solvent removed under vacuum. Purification by chromatography (30% ethyl acetate-hexanes) afforded (R,S)-ethyl (R,S)-3,4-dihydro-7-methylsulfomido-2H-1-benzopyran-2-carboxylate (3.21 g, 95%) as a clear oil: MS EI m/e 299 (M+); IR (film) 1730 cm−1; $^1$H NMR (CDCl$_3$) δ 1.29 (3H, t, J=7.24 Hz), 2.15–2.27 (2H, m), 2.68–2.79 (2H, m), 2.96 (3H, s), 4.26 (2H, q, J=7.25 Hz), 4.72 (1H, dd, J=7.14, 3.52 Hz), 6.77–6.82 (2H, m), 6.98 (1H, d, J=8.57 Hz).

To a solution of (R,S)-ethyl (R,S)-3,4-dihydro-7-methylsulfomido-2H-1-benzopyran-2-carboxylate (3.2 g, 10.69 mmol) in anhydrous tetrahydrofuran (30 mL) was added 10.1 mL of 2.0M lithium borohydride. the raction was allowed to stir at room temperature for 18 h then quenched by the slow addition of methanol. After 2 h water was slowly added (100 mL) and the reaction mixture extracted with diethyl ether (2×100 mL). The organic layer separated, dried over anhydrou magnesium sulfate, filtered, and the solvent removed under vacuum to afford (R,S)-3,4-dihydro-7-methylsulfonamido-2H-1-benzopyran-2-methanol as a clear oil: MS EI m/e 257 (M+); $^1$H NMR (CDCl$_3$) δ 1.77–1.99 (2H, m), 2.71–2.85 (2H, m), 3.00 (3H, s), 3.73–3.87 (2H, m), 4.10 (1H, m), 6.62–6.74 (2H, m), 7.00 (1H, d=7.91 Hz).

A solution of (R,S)-3,4-dihydro-7-methylsulfamido-2H-1-benzopyran-2-methanol (2.1 g, 8.16 mmol) and p-toluenesulfonyl chloride (2.33 g, 12.24 mmol), in anhydrous pyridine (20 mL) was allowed to stir for 24 h then poured into 1N aqueous HCl (100 mL). The reaction was then extracted with methylene chloride (350 mL) and the organic layer washed with 1N HCl (100 mL) followed by water (100 mL). The organic layer dried over anhydous magnesium sulfate, filtered, and the solvent removed under vacuum to afford a solid. Trituration with diethyl ether (30 mL) afforded (R,S)-3,4-dihydro-7-methylsulfonamido-2H-1-benzopyran-2-methyltosylate as a white solid, mp 170°–171° C.; MS EI m/e 411 (M+); $^1$H NMR (DMSO-d$_6$) δ 1.60 (1H, m), 1.86 (1H, m), 2.42 (3H, s), 2.55–2.72 (2H, m), 2.92 (3H, s), 4.13–4.28 (3H, m), 6.60 (1H, d, J=2.05 Hz), 6.68 (1H, dd, J=8.20, 2.05 Hz), 6.97 (1H, d, J=8.20 Hz), 7.48 (2H, d, J=8.06 Hz), 7.81 (2H, d, J=8.35 Hz), 9.58 (1H, s).

A mixture of (R,S)-3,4-dihydro-7-methylsulfamido-2H-1-benzopyran-2-methyltosylate (900 mg, 2.19 mmol), benzylamine (469 mg, 4.37 mmol), and triethylamine (221 mg, 2.19 mmol) in anhydrous dimethyl sulfoxide (15 mL) were allowed to stir at 80° C. for 18 h. The reaction was poured in water (150 mL) and extracted with metylene chloride (200 mL). The aqueous layer was made basic with aqueous saturated potassium carbonate and extracted with methylene chloride (150 mL). The combined organic layers were dried over magnesium sulfate, filtered, and the solvent removed under vacuum. Purification by chromatography (ethyl acetate) afforded 496 mg (65.4%) of a clear thick oil. The oxalate salt was prepared by the addition of the free base in a solution of tetrahydrofuran to an excess of oxalic acid in tetrahydrofuran: mp 232°–233° C.

Elemental analysis for $C_{18}H_{22}N_2SO_3.C_2H_2O_4$ Calc'd: C, 55.04; H, 5.54; N, 6.42 Found: C, 54.69; H, 5.51; N, 6.31

This general procedure utilizing 4-methylbenzylamine afforded:

(1b) N-{2-[(4-Methy-benzylamino)-methyl]-chroman-7-yl}-methanesulfonamide. The oxalate salt was prepared in tetrahydrofuran: mp 214°–215° C.

Elemental analysis for $C_{18}H_{22}N_2SO_3 \cdot C_2H_2O_4$ Calc'd: C, 63.50; H, 5.89; N, 3.90 Found: C, 62.97; H, 5.78; N, 3.81

The compounds of this invention are dopamine autoreceptor agonists, that is, they serve to modulate the synthesis and release of the neurotransmitter dopamine. They are thus useful for treatment of disorders of the dopaminergic system, such as schizophrenia, Parkinson's disease and Tourette's syndrome. Such agents are partial agonists at the postsynaptic dopamine $D_2$ receptor and are thereby useful in the treatment of alcohol and drug addiction.

Affinity for the dopamine autoreceptor was established by a modification of the standard experimental test procedure of Seemen and Schaus, European Journal of Pharmacology 203: 105–109, 1991, wherein homogenized rat striatal brain tissue is incubated with $^3$H-quinpirole (Quin.) and various concentrations of test compound, filtered and washed and counted in a Betaplate scintillation counter.

High affinity for the dopamine D-2 receptor was established by the standard experimental test procedure of Fields, et al., Brain Res., 136, 578 (1977) and Yamamura et al., eds., Neurotransmitter Receptor Binding, Raven Press, N.Y. (1978) wherein homogenized limbic brain tissue is incubated with $^3$H-spiroperidol (Spiper.) and various concentrations of test compound, filtered and washed and shaken with Hydrofluor scintillation cocktail (National Diagnostics) and counted in a Packard 460 CD scintillation counter.

The results of the tests with compounds representative of this invention are given in the immediately following table. Analogous compounds devoid of the 7-methylsulfonamido group are exemplified in the next table, to illustrate the markedly improved agonistic potency attending the 7-methylsulfonamido substituted modification in comparison with the products of Examples 1b and 1d, respectively.

an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carders include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carders are used in sterile liquid form compositions for parenteral administration.

Liquid pharmaceutical compositions which are sterile solutions or suspensions can be utilized by, for example,

| Example No. | $IC_{50}(nM)$ D2 Quin. | $IC_{50}(nM)$ D2 Spiper. | $IC_{50}$ (nM) 5-$HT_{1a}$ | $IC_{50}$ (nM) $\alpha_1$ | Ratio |
|---|---|---|---|---|---|
| 1 | 30.0 | 2379 | 6.0 | 70.0 | 79 |
| 1b | 201 ± 84 | 7256 | 111 | 1000 | 36 |
| 1c | 184 | 4858 | 218 | 1422 | 26 |
| 2 | 17.7 | 719 | 104 | 2273 | 41 |
| 2b | 14.15 | 416 | 21 | 1158 | 29 |

| Structure | $IC_{50}(nM)$ D2 Quin. | $IC_{50}$ (nM) 5-$HT_{1a}$ | $IC_{50}$ (nM) $\alpha_1$ | Ratio |
|---|---|---|---|---|
| [structure: tetrahydronaphthalene-O-CH2-NH-CH2CH2CH2-OH] | 576.5 ± 117.5 | | | |
| [structure: tetrahydronaphthalene-O-CH2-NH-CH2-phenyl] | 115 | 119 | 630 | — |

Hence, the compounds of this invention effect the synthesis of the neurotransmitter dopamine and thus are useful in the treatment of dopaminergic disorders such as schizophrenia, Parkinson's Disease, Tourette's Syndrome, alcohol addiction, cocaine addiction, and addiction to analagous drugs.

Applicable solid carriers for pharmaceutical compositions containing the compounds of this invention can include one or more substances which may also act as flavoring agents, lubricants, solubilizers, suspending agents, fillers, glidants, compression aids, binders or tablet-disintergrating agents or intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

What is claimed is:

1. A compound of formula I:

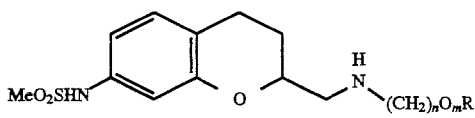

in which n is 1, 2 or 3;

m is 0 or 1; and

R is a substituted or unsubstituted phenyl group in which the substituents are, independently, one or two members selected from the group consisting of alkyl of 1 to 6 carbon atoms, hydroxy, halo and amino groups or R is alkyl of 1 to 6 carbon atoms or hydroxyalkyl of 1 to 6 carbon atoms;

or a pharmaceutically acceptable salt thereof.

2. A compound of claim 1 in which R is phenyl, tolyl or aminophenyl or a pharmaceutically acceptable salt thereof.

3. A compound of claim 1 in which n is 1, m is 0 and R is phenyl or tolyl or a pharmaceutically acceptable salt thereof.

4. The compound of claim 1 which is N-(2-{[3-(3-aminophenoxy)-propylamino]-methyl}-chroman-7-yl)-methanesulfonamide or a pharmaceutically acceptable salt thereof.

5. The compound of claim 1 which is N-{2-[3-hydroxy-propylamino)-methyl]-chroman-7-yl}-methansulfonamide or a pharmaceutically acceptable salt thereof.

6. The compound of claim 1 which is N-(2-propylaminomethyl-chroman-7-yl)-methanesulfonamide or a pharmaceutically acceptable salt thereof.

7. The compound of claim 1 which is N-(2-[benzylaminomethyl]-chroman-7-yl)-methanesulfonamide or a pharmaceutically acceptable salt thereof.

8. The compound of claim 1 which is N-(2-[[4-methylbenzyl]aminomethyl]-chroman-7-yl)-methanesulfonamide or a pharmaceutically acceptable salt thereof.

9. A pharmaceutical composition of matter comprising a compound of the formula:

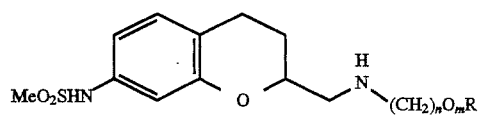

in which n is 1, 2 or 3;

m is 0 or 1; and

R is a substituted or unsubstituted phenyl group in which the substitutents are, independently, one or two members selected from the group consisting of alkyl of 1 to 6 carbon atoms, hydroxy, halo and amino groups or R is alkyl of 1 to 6 carbon atoms or hydroxyalkyl of 1 to 6 carbon atoms;

or a pharmaceutically acceptable salt thereof and a pharmaceutically acceptable carrier therefor.

10. A method for reducing dopamine synthesis and release in a patient suffering from hyperactivity of the dopaminergic systems, which comprises administering to said patient a compound of the formula:

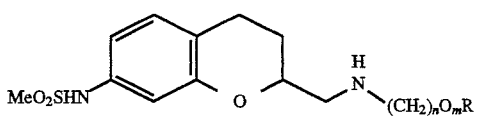

in which n is 1, 2 or 3;

m is 0 or 1; and

R is a substituted or unsubstituted phenyl group in which the substitutents are, independently, one or two members selected from the group consisting of alkyl of 1 to 6 carbon atoms, hydroxy, halo and amino groups or R is alkyl of 1 to 6 carbon atoms or hydroxyalkyl of 1 to 6 carbon atoms;

or a pharmaceutically acceptable salt thereof, in an amount sufficient to modulate the dopamine systems of the brain.

11. A method for treating schizophrenia which comprises administering to a patient suffering from schizophrenia, orally or parenterally, a compound of the formula:

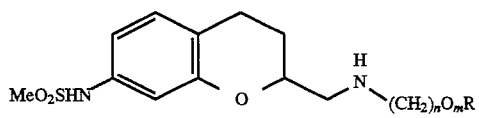

in which n is 1, 2 or 3;

m is 0 or 1; and

R is a substituted or unsubstituted phenyl group in which the substitutents are, independently, one or two members selected from the group consisting of alkyl of 1 to 6 carbon atoms, hydroxy, halo and amino groups or R is alkyl of 1 to 6 carbon atoms or hydroxyalkyl of 1 to 6 carbon atoms;

or a pharmaceutically acceptable salt thereof, in an amount sufficient to alleviate the symptoms of schizophrenia.

* * * * *